United States Patent [19]

Mochizuki et al.

[11] Patent Number: 5,078,855

[45] Date of Patent: * Jan. 7, 1992

[54] CHEMICAL SENSORS AND THEIR DIVIDED PARTS

[75] Inventors: Akihiko Mochizuki; Hideyo Iida, both of Tokyo, Japan

[73] Assignee: Taiyo Yuden Co., Ltd., Japan

[*] Notice: The portion of the term of this patent subsequent to May 1, 2007 has been disclaimed.

[21] Appl. No.: 257,381

[22] Filed: Oct. 13, 1988

[30] Foreign Application Priority Data

Oct. 13, 1987 [JP] Japan .................. 62-155625[U]
Jan. 25, 1988 [JP] Japan .................. 63-7103[U]

[51] Int. Cl.⁵ .................................. G01N 27/30
[52] U.S. Cl. ............................ 204/418; 204/412; 204/416; 357/25; 422/68.1; 422/82.01
[58] Field of Search ............ 357/25; 204/412, 416, 204/418, 153.1; 422/68.1, 82.01, 82.03, 82.02, 98

[56] References Cited

U.S. PATENT DOCUMENTS

| | | | |
|---|---|---|---|
| 4,508,613 | 4/1985 | Busta et al. | 357/25 X |
| 4,739,380 | 4/1988 | Lauks et al. | 357/25 |
| 4,764,797 | 8/1988 | Shaw et al. | 357/25 |
| 4,816,118 | 3/1989 | Oyama et al. | 357/25 X |
| 4,921,591 | 5/1990 | Mochizuki et al. | 357/25 X |

FOREIGN PATENT DOCUMENTS 63-128254  5/1988  Japan .

*Primary Examiner*—David A. Simmons
*Assistant Examiner*—Thi Dang
*Attorney, Agent, or Firm*—King & Schickli

[57] ABSTRACT

A chemical sensor includes a field effect-type transistor. An extended gate electrode is connected to a gate electrode of the transistor. A sensitive membrane is provided on at least a part of the extended gate electrode. The sensor also includes a reference electrode. Both the extended gate and reference electrodes are formed on a substrate different from the substrate on which the transistor is formed. Divided parts for the chemical sensor wherein the parts of the sensor except for the reference electrode are made independent are also disclosed and claimed. Sensors for simultaneously sensing a number of different chemical substances in a single sample are also disclosed and claimed.

7 Claims, 5 Drawing Sheets

CHEMICAL SENSORS AND THEIR DIVIDED PARTS

TECHNICAL FIELD

The present invention relates to a chemical sensor for sensing or detecting chemical species in solutions, using an extended gate type field-effect transistor and its divided part.

BACKGROUND OF THE INVENTION

In recent years, ion sensors and biosensors have been developed so as to measure the concentration of chemical species in liquid media to be examined. Such sensors are generally referred to as chemical sensors, and comprise a sensitive membrane to which a cyclic compound—called an ionophore—for specific binding to a chemical species to be measured, an enzyme for specifically catalyzing the reactions involved and like substances are fixed, and a transducer portion for transducing the quantity of the material specifically selected thereby into an electrical signal. Such chemical sensors have been applied to clinical, environmental, food and other inspections. As an example of one such transducer, an ion sensitive field-effect type transistor (hereinafter abbreviated as ISFET) is available.

This ISFET makes use of a change in electrical conductivity in the vicinity of a semiconductor surface, which occurs depending upon a change in the interfacial position of a sensitive membrane provided on the surface of the semiconductor and a solution.

Referring to the ISFET illustrated in FIG. 13, by way of example, a single crystal 1 of silicon is doped to form thereon a source electrode 2, a drain electrode 3 and a channel layer 4 located therebetween. An insulating layer 5 of $SiO_2$ is then provided over them to form a field-effect type transistor (hereinafter often abbreviated as FET). Further, a water-resistant and hydrogen ion-sensitive membrane 6 of $Si_3N_4$, etc. is deposited on the insulating film of $SiO_2$. As a gate voltage is impressed between the thus constructed assembly while immersed in a solution and a separate reference electrode provided therein through these films, a certain voltage is applied between the source electrode and the drain electrode to induce a carrier in the channel layer, thereby providing a drain current flow. An effective gate voltage is changed by the interfacial potential between the hydrogen ion sensitive film and the pH of the solution, whereby a change in the drain current can be detected.

However, the ISFET including the FET and the ion sensitive membrane made integral therewith has been incompatible in terms of the water resistance and sensitivity of the ion sensitive membrane, since an intended increase in the sensitivity results in a decrease in the water resistance and vice versa.

For that reason, there has also been known the so-called extended gate type ISFET wherein, as illustrated in FIGS. 14 and 15, a p type silicon substrate 11 is provided thereon with a $SiO_2$ layer, a signal transmission line 17 defined by an $InO_2$ film is formed at a position on the same substrate, which is different from the position of an FET portion 15 having drain, source and gate electrodes 12, 13 and 14, while it is connected to the gate electrode 14, and an ion sensitive portion, having ion sensitive membrane 16, etc. are formed on a part of the line 17. This extended gate type ISFET is used in combination with a separate reference electrode provided in a solution to be examined, while its ion-sensitive portion alone is immersed in that solution.

However, the extended gate type ISFET shown in FIGS. 14 and 15 incurs a rise in the production cost due to unsatisfactory efficiency of utilization of an expensive silicon substrate. This is because the ion-sensitive membrane portion that need not in principle be mounted on a silicon substrate and the FET portion that need be mounted on a silicon substrate are formed on the same silicon substrate.

Another problem with the ISFET of such a type is that it is unsuitable for the measurement of a slight quantity, i.e., about 0.05 to 0.1 ml of a sample under examination, as encountered in medical inspections.

A further problem with the extended gate type ISFET was that when it was used as a disposable chemical sensor by reason of the re-use of the sensitive membrane being unpreferred, the FET accounting for a substantial part of the cost of the chemical sensor was wasted, since the re-usable FET portion was discarded together with the membrane.

The chemical sensor need be of good accuracy and reproducibility. For that purpose, the properties of the FET must be uniform. To use a new FET for each measurement of a liquid under examination gives rise to a variation in the performance of the chemical sensor, since variations in the properties of the FET's produced are unavoidable. This leads to a still further problem that any data of good accuracy cannot be obtained.

One type of the extended gate type chemical sensor is disclosed in Japanese Patent Laid-Open Publication No. 63 (1988)—128254. According to this sensor, however, an FET portion of a measuring circuit is formed separately from an electrode portion to be immersed in a sample under examination, and is not of any flat structure.

SUMMARY OF THE INVENTION

A first object of the present invention is to provide a chemical sensor in which a part that need not be formed of a semiconductor substrate such as a silicon substrate can be formed of a separate, inexpensive substrate, and which can measure even a small amount of a sample.

A second object of the present invention is to provide a chemical sensor and its divided part in which an unrecyclable sensitive membrane portion is formed separately from other recyclable FET for disposal purposes.

DETAILED DESCRIPTION OF THE INVENTION

Figure 1:
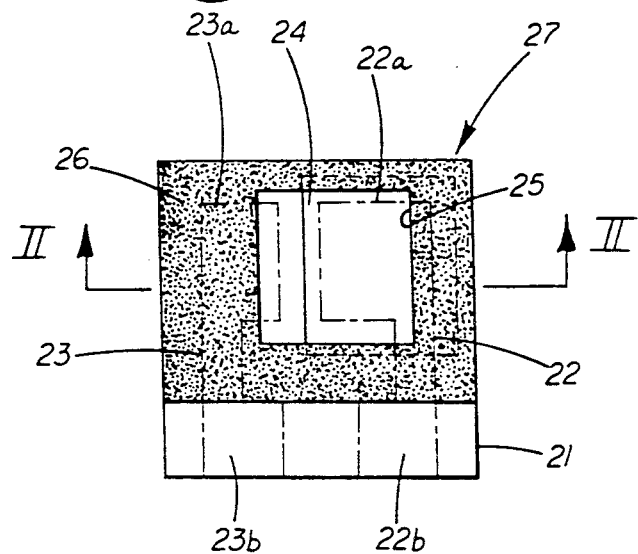
FIG. 1 is a plan view of an ion sensitive portion-containing chip that is a divided part of a first embodiment of the chemical sensor according to the present invention.
Figure 2:
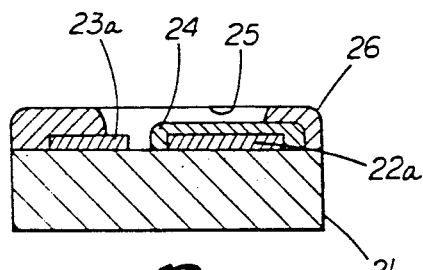
FIG. 2 is a sectional view taken along the line II—II of FIG. 1.

First, a glass substrate 21 is provided thereon with a silver electrode 22 for an extended gate and a silver electrode 23 for a reference electrode by vapor deposition, as illustrated in FIG. 1. These silver electrodes have a thickness of 0.5 to 1.0 um, and each are continuously provided with wide electrode bodies 22a and 23a at one end and connecting terminals 22b and 23b at the other end. A film of a vinyl chloride based resin containing valinomycin is then applied and coated on the entire surface of the electrode body 22a of the silver electrode 22 of an extended gate as an ion sensitive membrane, thereby forming a membrane 24 sensitive to potassium ions. Further, an epoxy base resin is coated on a portion of the thus obtained assembly except for a window opening 25 through which a sample is to be added dropwise, defined by a part of the potassium ion-sensitive membrane 24 and a portion of the electrode body 23a of the silver electrode 23 for a reference electrode, which faces thereto, thereby forming a water-resistant film 26. In this manner, an ion sensing chip is prepared, as generally shown at 27.

Figure 4:
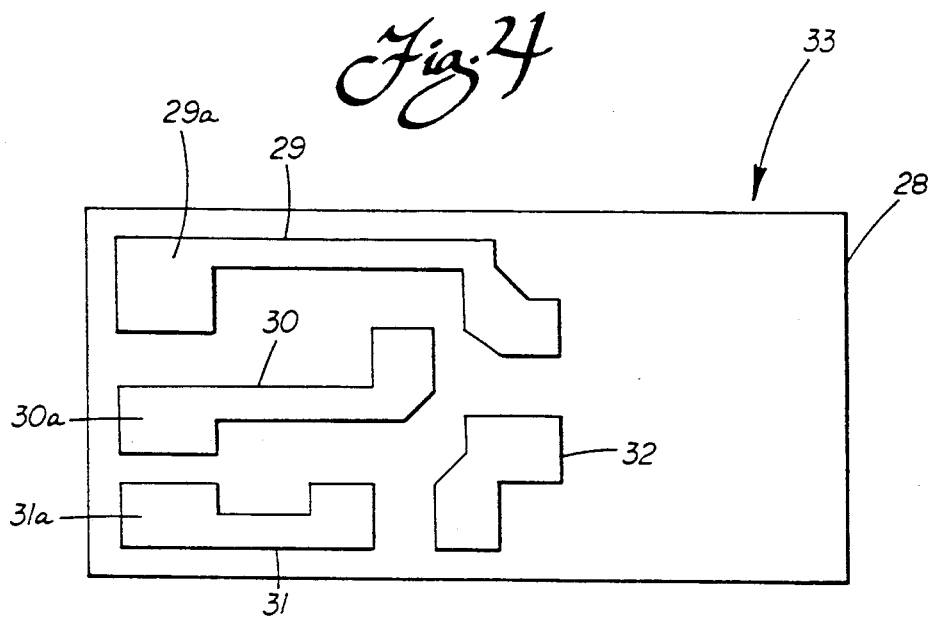
FIG. 4 is a plan view of a circuit board used with the first embodiment.

As illustrated in FIG. 4, on the other hand, a circuit board 33 on which a lead piece 29 for a reference electrode, a lead piece 30 for a source electrode, a lead piece 31 for a drain electrode and a lead piece 32 for a gate electrode are formed by etching of copper foils on a substrate 28 of glass fiber reinforced resin.

Figure 3:
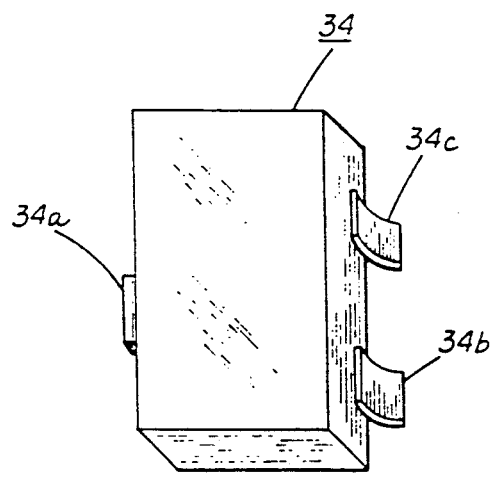
FIG. 3 is a perspective view of an FET.
Figure 5:
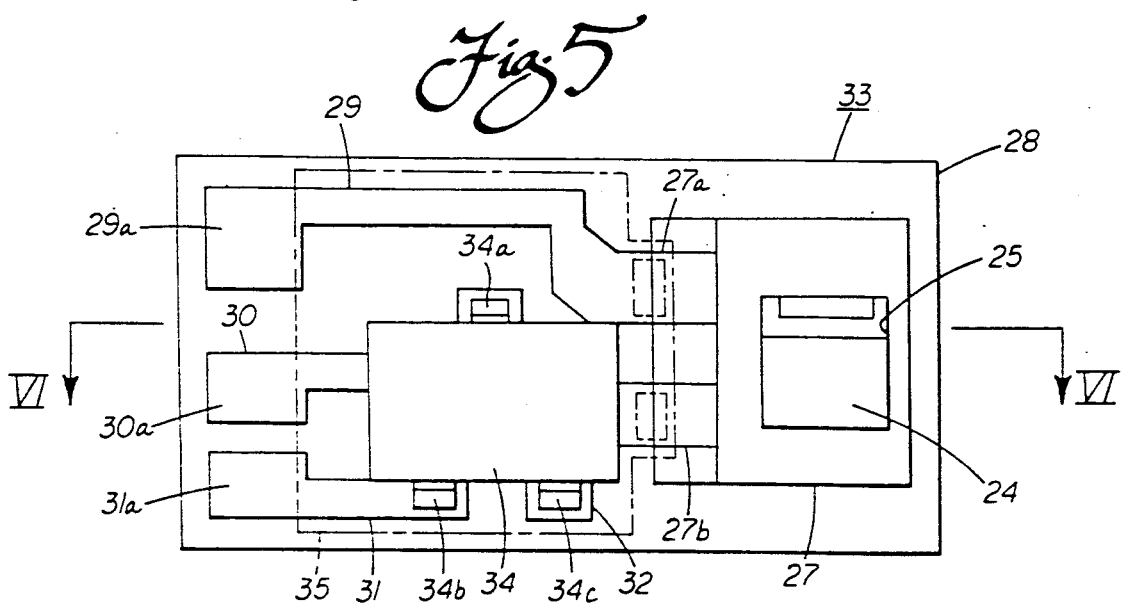
FIG. 5 is a plan view showing that circuit board into which the ion sensitive portion and FET are incorporated.

A commercially available FET (2-SK304) 34 including thereon a source electrode terminal 34a, a drain electrode terminal 34b and a gate electrode terminal 34c, as shown in FIG. 3, are electrically connected and fixed to the corresponding lead pieces 30, 31 and 32 for source, drain and gate electrodes on said circuit board 33, as illustrated in FIG. 5.

Figure 6:
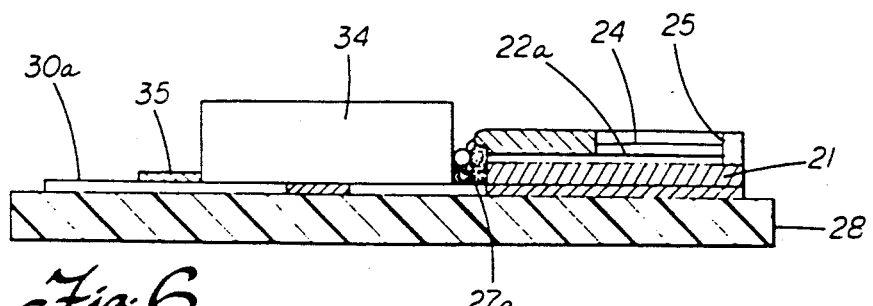
FIG. 6 is a sectional view taken along the line VI—VI of FIG. 5.

In order to mount the ion sensing chip 27 shown in FIG. 1 on said circuit board 33, connections are made between the lead piece 29 for a reference electrode and the connecting terminal 23b and between the lead piece 32 for a gate electrode and the connecting terminal 22b by means of an electrically conductive bonding agent (e.g., one composed mainly of carbon powders and a resin) 27a. After that, an epoxy resin film 35 is entirely coated on an exposed wiring portion of said circuit board except for the connecting terminals 29a, 30a, 31a and 32a of said lead pieces 29, 30, 31 and 32 for comparison, source, drain and gate electrodes, respectively. In this manner, a potassium ion sensor is obtained, as illustrated in FIG. 6.

Figure 7:
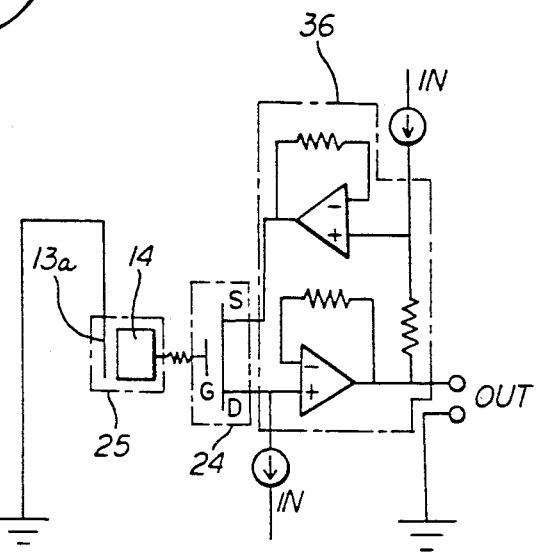
FIG. 7 is a diagram of a measuring circuit using an ISFET.

This potassium ion sensor was connected to a source follower circuit 36, shown in FIG. 7, and a potassium ion-containing solution was added dropwise thereto through the window opening 25 as a sample to record the resulting output voltage. As a result, an output voltage proportional to a potential change on the surface of the ion sensitive membrane was obtained. At that time, the sensitivity in potassium ions was about 51 mV (51 mV/pK) for a ten-fold change in ion activity, and made no difference to that of the ion sensitive field-effect type transistor sensors heretofore reported.

It is understood that while the foregoing embodiment has been described with the ion sensing chip, the ion sensitive portion may be provided directly on the circuit board, facing to the window opening for the dropwise addition of a sample, as is the case with the foregoing embodiment.

More specifically, the lead pieces 29 and 32 for reference and gate electrodes may be extended in FIG. 4 to form reference and gate electrodes corresponding to the silver electrodes 23 and 22 for a reference electrode and an extended gate, respectively. Then, an ion sensitive portion is formed, which is of a similar structure comprising the potassium ion sensitive membrane 24 of FIG. 1, the window opening for the dropwise addition of a sample, located at a position facing thereto, and the water-resistant film 26, and the FET 24 is mounted on that portion in a similar manner as explained in connection with FIG. 5. Since such an arrangement dispenses with any connection with the electrically conductive bonding agent 27a, as shown in FIG. 6, it is possible to increase the reliability of measurements to a higher level.

Figure 8:
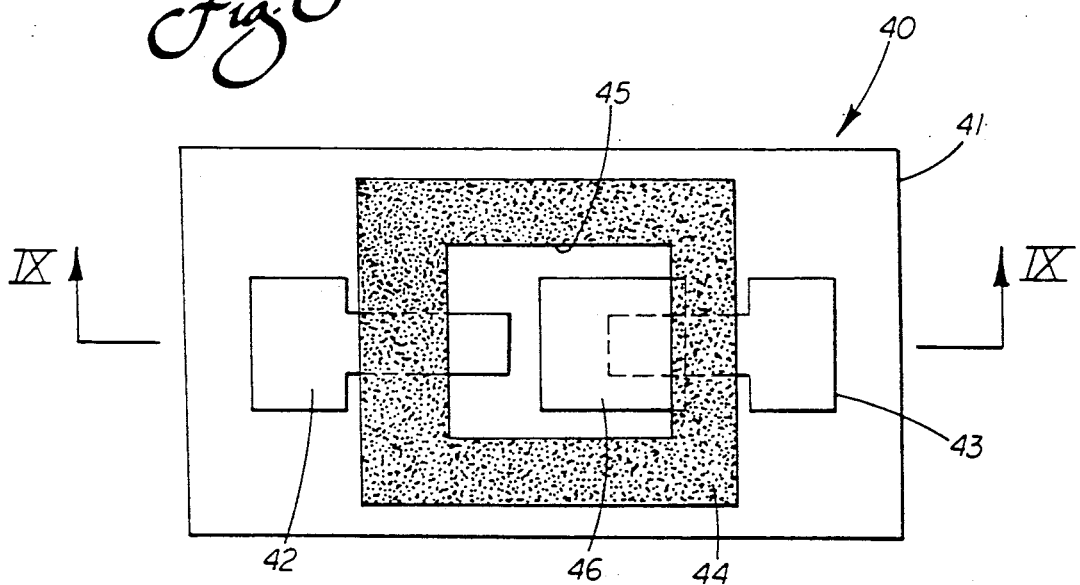
FIG. 8 is a plan view of an ion sensing plate that is a divided part of a second embodiment of the chemical sensor according to the present invention.
Figure 9:
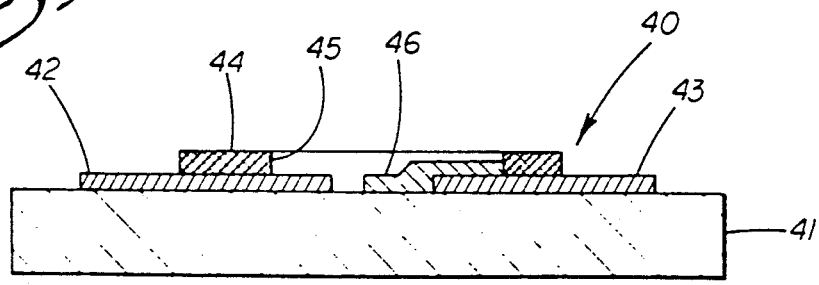
FIG. 9 is a sectional view taken along the line IX—IX of FIG. 8.

It is also understood that while the foregoing embodiment has been described with the ion sensing chip being mounted on the circuit board along with the FET, an ion sensing portion-containing plate 40 as shown in FIG. 8, may be provided for use in combination with the FET.

More specifically, said ion sensing plate 40 may be prepared by screen-printing with a paste of a composite of silver and platinum and a composite of silver and palladium on an alumina substrate of 0.5 mm in thickness and burning them together to form a reference electrode 42 and an electrode 43 for an extended gate, which are linearly spaced away from each other.

A frame-like bank body 44 of a glass layer is then formed on the assembly except for both ends and opposite portions of the reference electrode 42 and the electrode 43 for an extended gate to form a window opening 45 through which a sample is to be added dropwise.

Further, an ion sensitive membrane 46 comprising a vinyl chloride resin based film containing valinomycin is formed on the electrode 43 for an extended gate made to face to said window opening 45 by coating and drying of a coating material therefor.

Figure 10:
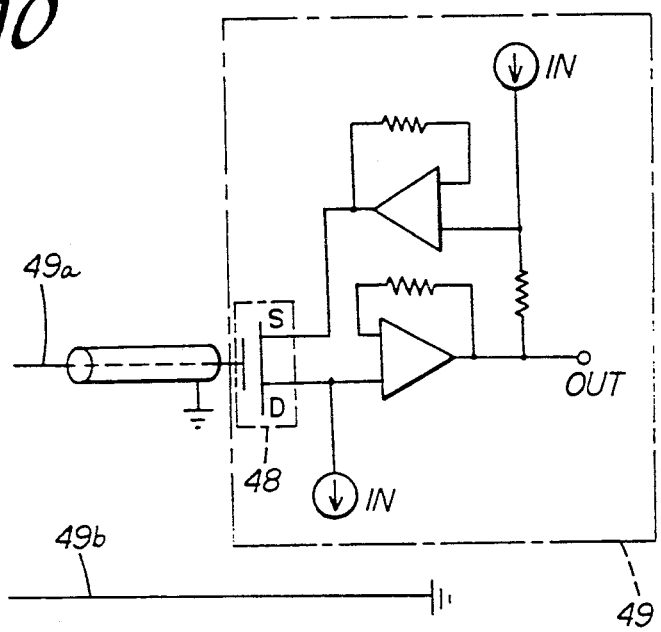
FIG. 10 is a diagram of a measuring circuit in the chemical sensor using the ion sensing plate according to the second embodiment.

The potassium ion sensing plate is prepared in this manner, and may be used, while the outer terminals of the reference electrode 42 and the electrode 43 for an extended gate are connected with, e.g., leads 49a and 49b for an extended gate and a reference electrode of a measuring circuit 49 which is shown in FIG. 10 and connected with a separately prepared FET 48 by way of a probe.

Fifty (50) ul of a potassium ion solution were actually added dropwise to the ion sensor of such a structure through the window opening 45 to determine the relation between the concentration and the output. As a result, a sensitivity of about 51 mV (51 mV/pK) was obtained for a ten-fold change in ion activity. It is noted that such determination was carried out in a shielded box, while a shielded wire was used for the lead 39a of the extended gate electrode including a prober, since the FET was susceptible to noise influences due to a high-impedance input.

The foregoing embodiment has been described with reference to the ion sensor for the measurement of potassium ions. However, if ion sensitive membranes carrying thereon ionophores stated in the following left column are used, it is then possible to measure specific components set forth in the following right column.

| Silicon Nitride Membrane | Hydrogen Ion |
| Bis-12-Crown-4/PVC | Sodium Ions |
| Tridecylamine/PVC | Chloroions, |
| | Hydrogen Ions |

It is also possible to prepare biosensors for measuring glucose, urea, etc. by immobilizing enzymes such as glucose oxidase, urease, etc. on a hydrogen ion electrode.

Figure 11:
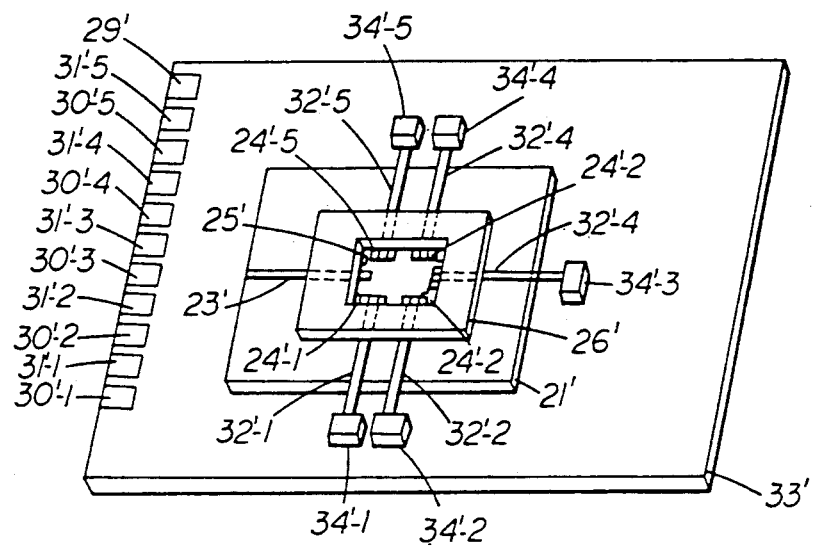
FIG. 11 is a perspective view of a third embodiment of the chemical sensor according to the present invention.
Figure 12:
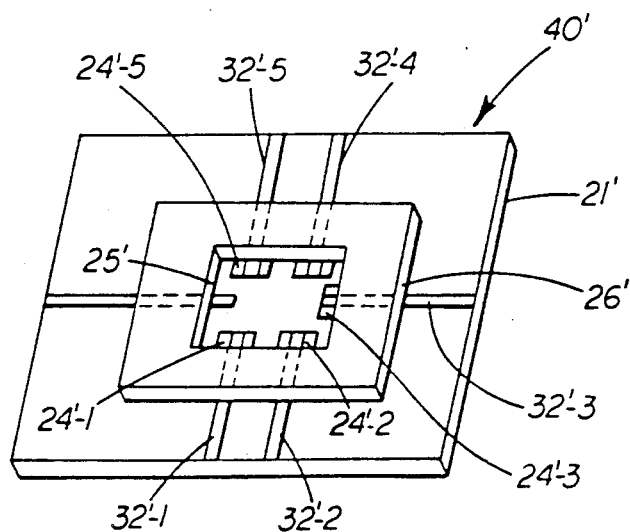
FIG. 12 is a divided part for that chemical sensor.
Figure 13:
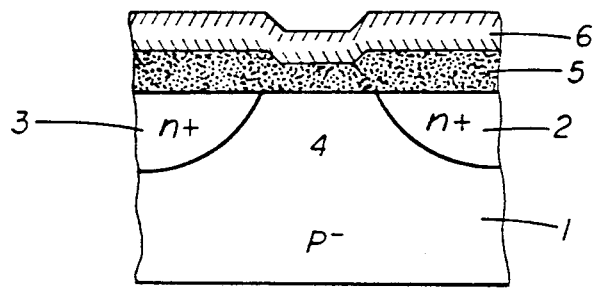
FIG. 13 is a sectional view of a conventional ISFET.
Figure 14:
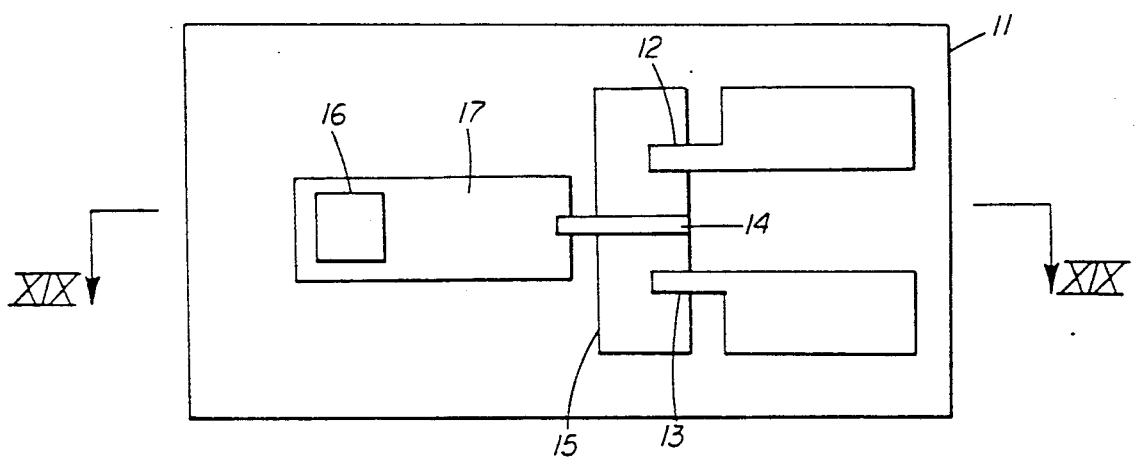
FIG. 14 is a plan view showing a main part of a conventional isolation gate type ISFET ion sensor, except for a resin coated film on the surface.
Figure 15:
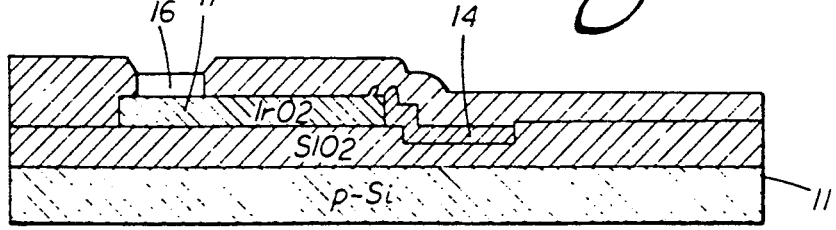
FIG. 15 is a sectional view taken along the line XIX—XIX of FIG. 14, showing the sensor having a resin film coated thereon.

According to the embodiments as described above, it is possible to measure only one component contained in sample liquids. As illustrated in FIGS. 11 and 12, however, a similar circuit board 33' as illustrated in FIG. 4 may be radially provided thereon with five sets of lead pieces for reference, source, drain and gate electrodes similar to those shown in FIG. 4, and the lead pieces of each set may be connected together in a similar manner as shown in FIG. 5 and provided with FET's 34'-1, 34'-2, 34'-3, 34'-4 and 34'-5. Then, extended gate pieces (extended gate electrodes) 32'-1, 32'-2, 32'-3, 32'-4 and 32'-5 are provided on a glass substrate 21' with the one ends being centrically concentrated, as shown in FIG. 11, and are soldered to the lead pieces for gate electrodes of the FET's. These extended gate pieces are provided thereon with a bank body 26' of an epoxy resin to form a window opening 25' through which a sample is to be added dropwise. Further, the extended gate pieces are provided with ion sensitive membranes 24'-1, 24'-2, 24'-3, 24'-4 and 24'-5 carrying thereon such different ionophores as mentioned above.

It is noted that reference numeral 23' stands for a reference electrode having its end located in the window opening 25'. It is also noted that reference numerals 30'-2 to 30'-5 indicate source electrode terminals, 31'-1 to 31'-5 drain electrode terminals and 29' a reference electrode terminal. Connecting wires between the FET's and the reference electrode are coated on their surfaces with an insulating film, although not illustrated.

In the foregoing embodiment, the FET's and the window opening through which a sample is to be added dropwise are formed on the same substrate. However, the assembly of FIG. 12 may be used as a divided part 40', which is in turn connected to the associated parts, as illustrated in FIG. 11. In that case, the divided part 40' may be connected to the FET's and reference electrode terminal by insertion or like means.

Such a divided part may be replaced separately from the FET's.

In the foregoing embodiments, silver is used for the extended gate electrode. However, metals such as gold, platinum, chromium and copper, oxide conductors such as $IrO_2$ and $SnO_2$ or silver/silver chloride may be used for the extended gate, gate, reference, source and drain electrodes. Glass, resin and ceramic substrates may be used for the substrate on which an extended gate electrode is formed as well as the circuit board.

Although the FET's and the measuring circuits of FIGS. 7 and 10 may be formed on the same substrate, they may be provided on separate substrates and connected together for use. In that case, the divided parts of the chemical sensors shown in FIGS. 1 and 8 may be inserted into the FET-mounted substrate or a substrate including both the FET's and the measuring circuit for connection thereto.

According to the present invention, a substrate different from a field-effect type transistor substrate is provided with at least an extended gate of two parts consisting of an extended gate and a reference electrode, and the extended gate is provided with a sensitive membrane to connect it with a field-effect type transistor for use. Thus, an inexpensive material such as glass, resin, ceramic and stainless plates may be used for a substrate on which the extended gate is to be provided. The amount of a sample required for measurement can also be reduced, since the provision of the extended gate and reference electrode on the same substrate makes it possible to carry out such measurement, using the sample in such an amount that the sensor need only be wetted.

According to the present invention, the extended gate on which a sensitive membrane is formed and provided on a substrate with or without a reference electrode may be used as an independently functioning part for a biosensor or ion sensor, i.e., a chemical sensor. The chemical sensor of the present invention is thus economical by reason of the fact that the part, which comes in contact with and is contaminated by a sample, (and as such is not appropriate for re-use), is disposable separately from an expensive field-effect type transistor which forms another part of the sensor body and is recyclable. At the same time, it is possible to obtain data of limited variations and measurements of improved accuracy.

We claim:

1. A chemical sensor, comprising:
    a first substrate provided with a field-effect type transistor including a gate electrode;
    a second substrate including an extended gate electrode and a reference electrode, said extended gate electrode being connected to said gate electrode; and
    a sensitive membrane provided on at least a part of said extended gate electrode whereby a component of a sample is sensed and detected.

2. A chemical sensor as claimed in claim 1, wherein said second substrate is a plate formed from material selected from a group consisting of glass, resin and ceramic.

3. A chemical sensor as claimed in claim 1, wherein said second substrate, extended gate electrode and reference electrode form a sensing chip and further including a circuit board having wiring for connecting said sensing chip and said field-effect type transistor, said sensing chip and field-effect type transistor being arranged on and connected to said circuit board.

4. A chemical sensor as claimed in claim 1 further including a bank body for surrounding portions of said extended gate and reference electrodes on said second substrate, said bank body forming a window opening through which a sample under examination is to be added dropwise.

5. A chemical sensor as claimed in claim 1, wherein:
a plurality of field-effect type transistors including gate electrodes are formed on said first substrate;
a plurality of extended gate electrodes and reference electrodes are provided on said second substrate, said extended gate electrodes being connected to said gate electrodes; and
a plurality of membranes sensitive to different chemical substances provided on at least a portion of said extended gate electrodes whereby a plurality of components on a sample may be simultaneously sensed and detected.

6. A sensing chip for connection to a field-effect type transistor on an independent substrate comprising:
a substrate formed from material selected from a group consisting of glass, resin and ceramic;
an extended gate electrode and reference electrode provided on said substrate, a part of said extended gate electrode being in opposition to a part of said reference electrode on said substrate;
a sensitive membrane coating said part of said extended gate electrode; and
a bank body for surrounding portions of said extended gate electrode and reference electrode, said bank body forming a window opening through which a sample under examination may be added dropwise;
said sensing chip being connected to said field-effect type transistor on a separate, independent substrate whereby a component of a sample may be sensed.

7. A sensing chip as claimed in claim 6, wherein:
a plurality of extended gate electrodes and reference electrodes are provided on said substrate; and
a plurality of membranes sensitive to different chemical substances on at least a portion of said extended gate electrodes whereby a plurality of components of a sample may be simultaneously sensed.

* * * * *